US012796893B2

(12) United States Patent
Park et al.

(10) Patent No.: US 12,796,893 B2
(45) Date of Patent: Nov. 17, 2026

(54) DETACHABLE ENDOSCOPE

(71) Applicant: TAEWOONG MEDICAL CO., LTD., Gimpo-si (KR)

(72) Inventors: Sung Hwan Park, Seoul (KR); Hyun Soo Ji, Seoul (KR)

(73) Assignee: TAEWOONG MEDICAL CO., LTD., Gimpo-si (KR)

( * ) Notice: Subject to any disclaimer, the term of this patent is extended or adjusted under 35 U.S.C. 154(b) by 389 days.

(21) Appl. No.: 18/155,333

(22) Filed: Jan. 17, 2023

(65) Prior Publication Data

US 2023/0225587 A1 Jul. 20, 2023

(30) Foreign Application Priority Data

Jan. 14, 2022 (KR) ........................ 10-2022-0006184

(51) Int. Cl.

*A61B 1/00* (2006.01)
*A61B 1/005* (2006.01)

(52) U.S. Cl.

CPC ...... *A61B 1/00105* (2013.01); *A61B 1/00128* (2013.01); *A61B 1/00154* (2013.01); *A61B 1/0057* (2013.01)

(58) Field of Classification Search

CPC ..... A61B 1/005; A61B 1/0051; A61B 1/0052; A61B 1/0053; A61B 1/0055; A61B 1/0056; A61B 1/0057; A61B 1/0058; A61B 1/00066; A61B 1/00105; A61B 1/00128; A61B 1/00154

See application file for complete search history.

(56) References Cited

U.S. PATENT DOCUMENTS 7,008,376 B2 * 3/2006 Ikeda .................. A61B 1/0051 600/152
8,070,685 B2 * 12/2011 Harhen .................... A61B 8/12 604/95.04
11,642,006 B2 * 5/2023 Shin ..................... A61B 1/0052 600/136
11,642,007 B2 * 5/2023 Shin ................... A61B 1/00105 600/136
11,998,171 B2 * 6/2024 Shin ................... A61B 1/00066

(Continued)

FOREIGN PATENT DOCUMENTS

JP H03-111024 A 5/1991
JP 2000014628 A * 1/2000

(Continued)

OTHER PUBLICATIONS

Isamu Watanabe, "Office Action for Japanese Application 2023-003681", Jan. 9, 2024, JPO, Japan.

*Primary Examiner* — Ryan N Henderson
(74) *Attorney, Agent, or Firm* — Bridgeway IP Law Group, PLLC; Jihun Kim

(57) ABSTRACT

A detachable endoscope including: an insertion unit whose one end is to be inserted into a body; an operation unit coupled to another end of the insertion unit and operating the one end of the insertion unit to perform a bending motion using an operation module; and a detachment unit which detachably couples the operation unit and the insertion unit, and locks the insertion unit in a coupled state simultaneously when being coupled, so that the insertion unit is secured to the operation unit.

4 Claims, 9 Drawing Sheets

(56) References Cited

U.S. PATENT DOCUMENTS

| | | | | |
|---|---|---|---|---|
| 2006/0235304 | A1* | 10/2006 | Harhen | A61B 8/12 600/459 |
| 2006/0276775 | A1* | 12/2006 | Rosenberg | A61B 17/0469 606/1 |
| 2007/0238927 | A1* | 10/2007 | Ueno | A61B 1/00105 600/152 |
| 2008/0125628 | A1* | 5/2008 | Ueno | G02B 23/2453 600/130 |
| 2008/0249365 | A1* | 10/2008 | Masaki | A61B 1/0016 600/152 |
| 2008/0287738 | A1* | 11/2008 | Adachi | A61B 1/0016 600/118 |
| 2010/0268031 | A1* | 10/2010 | Koyama | A61B 1/0051 600/146 |
| 2012/0100729 | A1* | 4/2012 | Edidin | H01R 13/622 439/38 |
| 2012/0197190 | A1* | 8/2012 | Suon | A61M 25/0133 604/95.04 |
| 2020/0077874 | A1* | 3/2020 | Long | A61B 1/015 |
| 2021/0068619 | A1* | 3/2021 | Shin | A61B 1/0669 |
| 2021/0068621 | A1* | 3/2021 | Shin | A61B 1/00073 |
| 2021/0068624 | A1* | 3/2021 | Shin | A61B 1/06 |
| 2021/0068625 | A1* | 3/2021 | Shin | A61B 1/0057 |
| 2021/0068626 | A1* | 3/2021 | Shin | A61B 1/00105 |
| 2021/0093166 | A1* | 4/2021 | Shin | A61B 1/053 |
| 2021/0100429 | A1* | 4/2021 | Chu | A61B 1/00103 |
| 2021/0113068 | A1* | 4/2021 | Shin | A61B 1/0055 |
| 2021/0145257 | A1* | 5/2021 | Levinson | A61B 1/00066 |
| 2021/0361143 | A1* | 11/2021 | Wang | A61B 1/0052 |
| 2022/0265967 | A1* | 8/2022 | Alhadeff | A61B 1/00105 |
| 2022/0304549 | A1* | 9/2022 | Iijima | A61B 1/00105 |
| 2023/0011670 | A1* | 1/2023 | Kohanfars | A61B 1/00119 |
| 2023/0023094 | A1* | 1/2023 | Dixson | A61B 1/00042 |
| 2023/0172433 | A1* | 6/2023 | Levinson | A61B 1/015 600/109 |

FOREIGN PATENT DOCUMENTS

| | | | |
|---|---|---|---|
| JP | 2004-000427 | A | 1/2004 |
| JP | 2021-041155 | A | 3/2021 |
| JP | 2021-041159 | A | 3/2021 |
| JP | 2021-514717 | A | 6/2021 |
| JP | 2021-514743 | A | 6/2021 |
| KR | 102161974 | B1 * | 9/2020 |

* cited by examiner

DETACHABLE ENDOSCOPE

CROSS REFERENCE TO RELATED APPLICATION

The present application claims priority to Korean Patent Application No. 10-2022-0006184, filed Jan. 14, 2022, the entire contents of which is incorporated herein for all purposes by this reference.

BACKGROUND OF THE INVENTION

Field of the Invention

The present disclosure relates to a device, and more particularly to a detachable endoscope.

Background Art

In general, a medical procedure using an endoscope is to insert an endoscope equipped with a camera and a medical procedure tool through a small hole without making a large incision in the body of a patient, and then proceed with the procedure while observing the affected part of the patient through the image taken by the endoscope in the body. In particular, the endoscopic procedure starting from laparoscopic surgery has advantages in that the incision region is smaller than that of laparotomy, so the scar region is also small, and there is little bleeding, which leads to the quick patient recovery after the procedure.

The conventional endoscopes are integrally constituted with an insertion part intended to be inserted into the human body and an operation part that operates the insertion part, and a plurality of channels and guides are embedded through the inside of each part. In particular, an image sensing device such as an expensive CCD is provided at the front end of the insertion part inserted into the body. Therefore, it is difficult to separate only the insertion part from the operation part and replace it with a new one. To overcome this problem, in line with the trend of strengthening the sanitary function of medical endoscopes, various types of detachable endoscopes are being used in which an insertion part intended to be inserted into the body and an operation part for operating the insertion part are connected to each other when being used, or separated from each other when being stored.

However, in the conventional detachable endoscope having a structure in which the operation part and the insertion part are detachably coupled via the connection part, in order to separate the insertion part and the operation part from each other by releasing the engagement in the connection part after the endoscopic procedure, a pressing member such as a button must be provided in the connection part, and the engagement connection in the connection part must be released using this pressing member. Therefore, the structure of the connection part that detachably connects the operation part and the insertion part to each other becomes very complicated, and the manufacturing cost of the endoscope increases.

Further, the overall number of components provided in the connection part of the endoscope increases due to the engagement release button and accessory structures associated therewith additionally provided in the connection part. In the case of a mechanical malfunction of the engagement release button, the endoscope for a medical procedure cannot be used, while the cost required to maintain/repair the connection part increases.

SUMMARY OF THE INVENTION

A technical problem to be addressed by the present disclosure is to provide a detachable endoscope that prevents internal contamination of the endoscope and allows easy replacement and cleaning of a part intended to be inserted into the human body by configuring the detachable endoscope such that the part can be secured simultaneously when being coupled.

Technical drawbacks, which the present disclosure is to address, are limited to the aforementioned ones, and unmentioned or other technical drawbacks may be clearly appreciated from the following detailed description by a person having ordinary skill in the art to which the present disclosure belongs.

In order to achieve the above technical objects, a detachable endoscope according to an embodiment of the present disclosure may include an insertion unit whose one end is to be inserted into a body; an operation unit coupled to another end of the insertion unit and operating the one end of the insertion unit to perform a bending motion using an operation module; and a detachment unit which detachably couples the operation unit and the insertion unit, and locks the insertion unit in a coupled state simultaneously when being coupled, so that the insertion unit is secured to the operation unit.

According to an example of the present disclosure, the detachment unit may include a first detachment module disposed at one end of the operation unit and having an intermediate connection part to which a connection wire receiving a force from the operation module is connected; and a second detachment module disposed at the other end of the insertion unit, detachably coupled to the first detachment module, and having an insertion end connection part connected to an operation wire that transfers a force applied by the operation module to the one end of the insertion unit.

According to an example of the present disclosure, the intermediate connection part may be provided with an intermediate connection body disposed rotatably around a longitudinal direction; an insertion groove formed concavely inward in a longitudinal direction at one end of the intermediate connection body and having a penetration part penetratingly formed in a direction perpendicular to the longitudinal direction; and a guide projection for guiding rotational motion of the intermediate connection body, and the insertion end connection part may be provided with an insertion end connection body extending in a longitudinal direction; and an engaging member protruding outward in a longitudinal direction from one end of the insertion end connection body.

According to an example of the present disclosure, when the insertion unit and the operation unit are coupled, the engaging member may be inserted into the insertion groove, the engaging member being protrudingly formed in a length corresponding to the concave depth of the insertion groove.

According to an example of the present disclosure, when the insertion unit and the operation unit are coupled, the insertion end connection part may press the intermediate connection part in a longitudinal direction in a state in which one end of an insertion end connection body is in contact with one end of the intermediate connection body.

According to an example of the present disclosure, as the insertion end connection body rotates along the guide projection by the pressing of the intermediate connection part, the engaging member may be inserted into the penetration part to be in an engaged state.

According to an example of the present disclosure, the intermediate connection part and the insertion end connection part may be arranged on a same line along a longitudinal direction to face each other, be coupled to each other, and operate integrally based on manipulation of the operation module.

In the detachable endoscope according to the embodiments of the present disclosure, the insertion unit intended to be inserted into the human body is configured to be detachable from the operation unit, so that the internal contamination of the endoscope can be prevented and parts can be easily replaced and cleaned. Additionally, in the course of coupling the insertion unit, one end of the insertion unit can be inserted into and pressed against one end of the operation unit, and at the same time, engaged, coupled, and locked therewith, without the use of a separate engaging or locking structure, thereby enabling simple and easy assembly and disassembly of the insertion unit.

The effects of the present disclosure are not limited to the aforementioned effects, but should be understood as including all effects that can be inferred from the configuration provided by the description or claims of the present application.

DETAILED DESCRIPTION OF THE INVENTION

Figure 1:
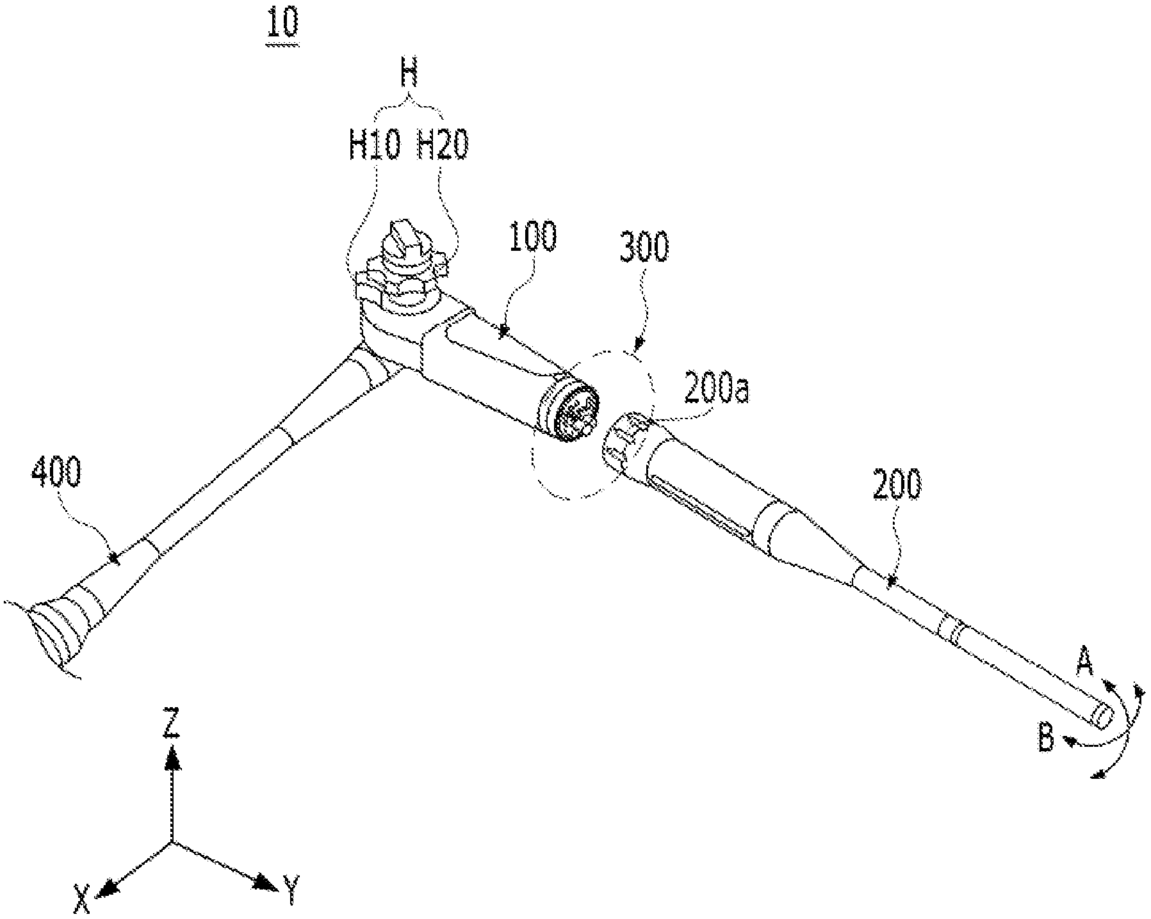
FIG. 1 is a perspective view showing a detachable endoscope according to an embodiment of the present disclosure.

Hereinafter, embodiments of the present disclosure will be described with reference to the accompanying drawings. However, the disclosure can be embodied in various different forms, and the scope of the disclosure should not be construed as being limited to the embodiments described herein. In the drawings, in order to describe clearly the disclosure, parts not related to the description are omitted, and like reference signs will be given to like constitutional elements throughout the specification.

As used herein, "connecting (or combining)" a part with another part (or "bring" a part into contact or touch with another part) may refer to a case where they are "indirectly connected" to each other with other element intervening therebetween, as well as a case where they are "directly connected". Further, when a part "includes (or comprises)" a component, it means not that the part excludes other component, but instead that the part may further include other component unless expressly stated to the contrary.

The terms used herein are used to merely describe specific embodiments, but are not intended to limit the disclosure. Singular expressions may include the meaning of plural expressions unless the context clearly indicates otherwise. The terms such as "include (or comprise)", "have (or be provided with)", and the like are intended to indicate that features, numbers, steps, operations, components, parts, or combinations thereof written in the following description exist, and thus should not be understood as that the possibility of existence or addition of one or more different features, numbers, steps, operations, components, parts, or combinations thereof is excluded in advance.

Hereinafter, embodiments of this disclosure will be described in detail with reference to the accompanying drawings.

Figure 2:
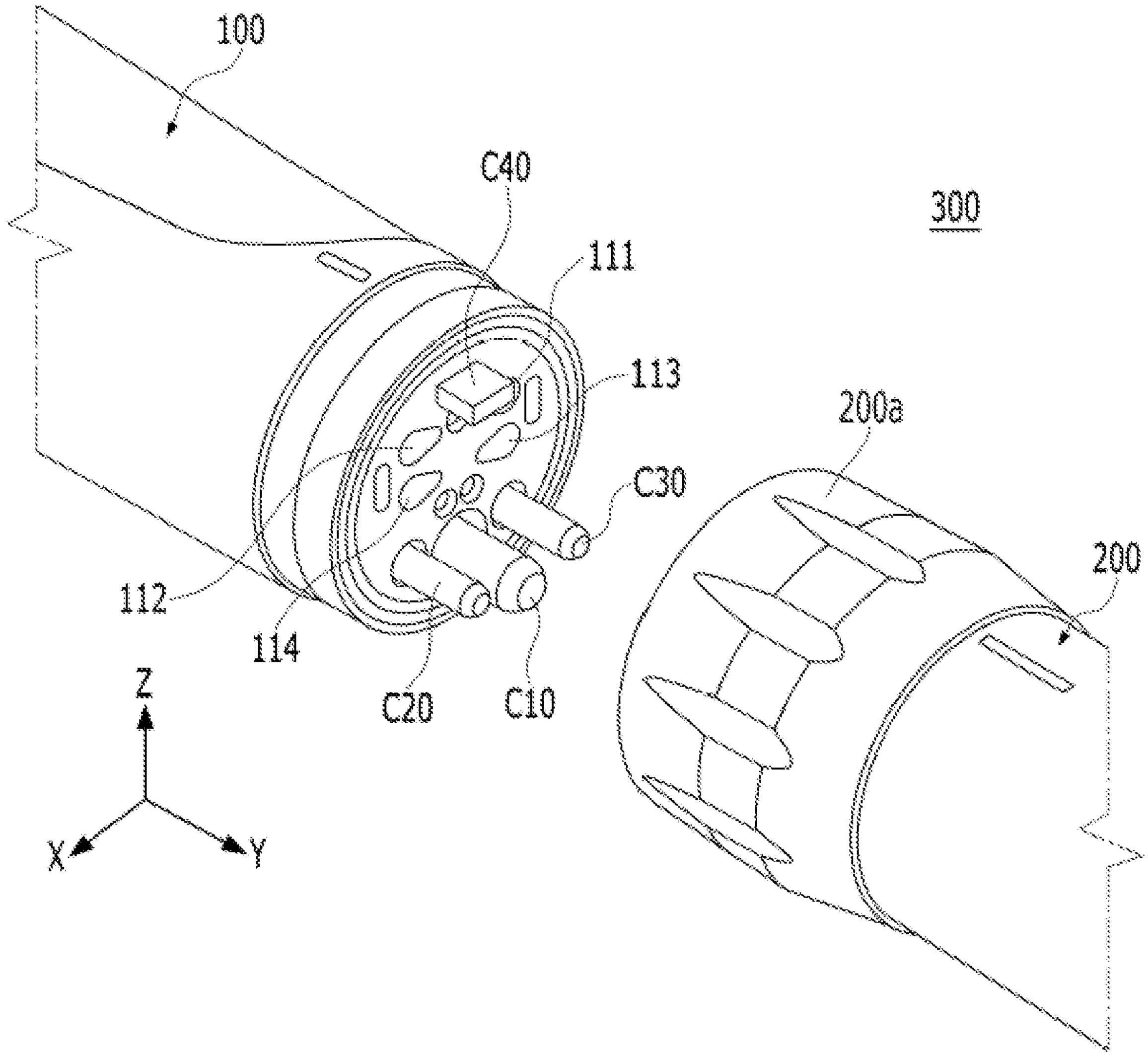
FIG. 2 is a perspective view illustrating a detachment unit which couples an insertion unit and an operation unit that are provided in a detachable endoscope according to an embodiment of the present disclosure.
Figure 3:
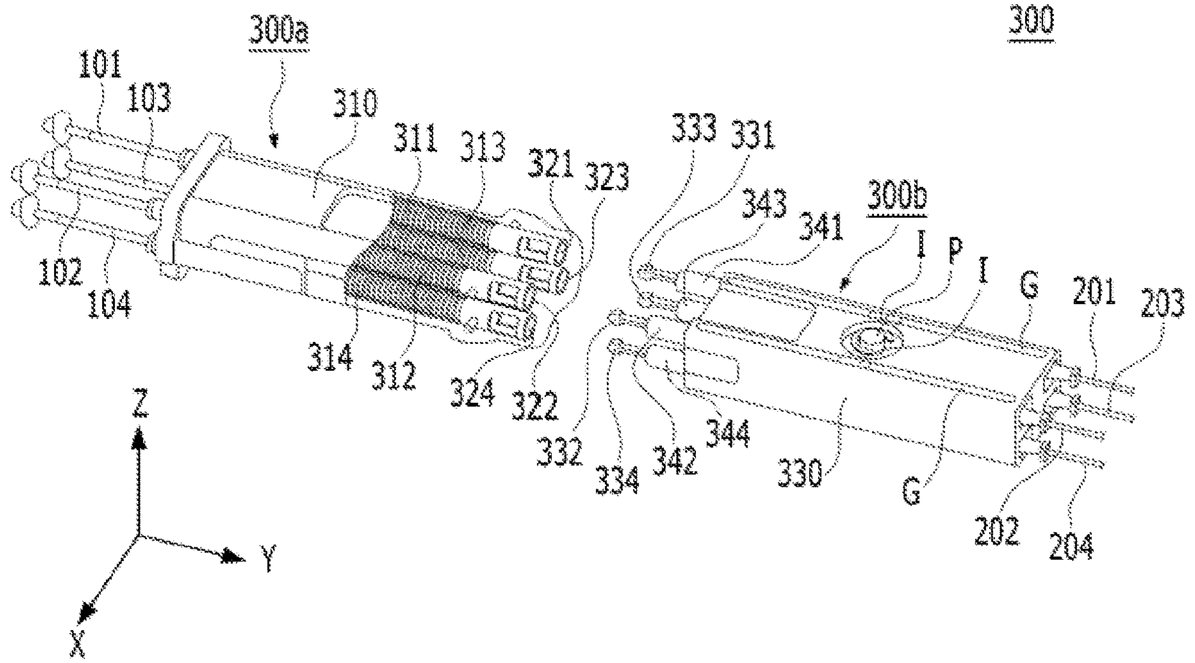
FIG. 3 is a perspective view showing a detachment unit provided in a detachable endoscope according to an embodiment of the present disclosure.
Figure 4:
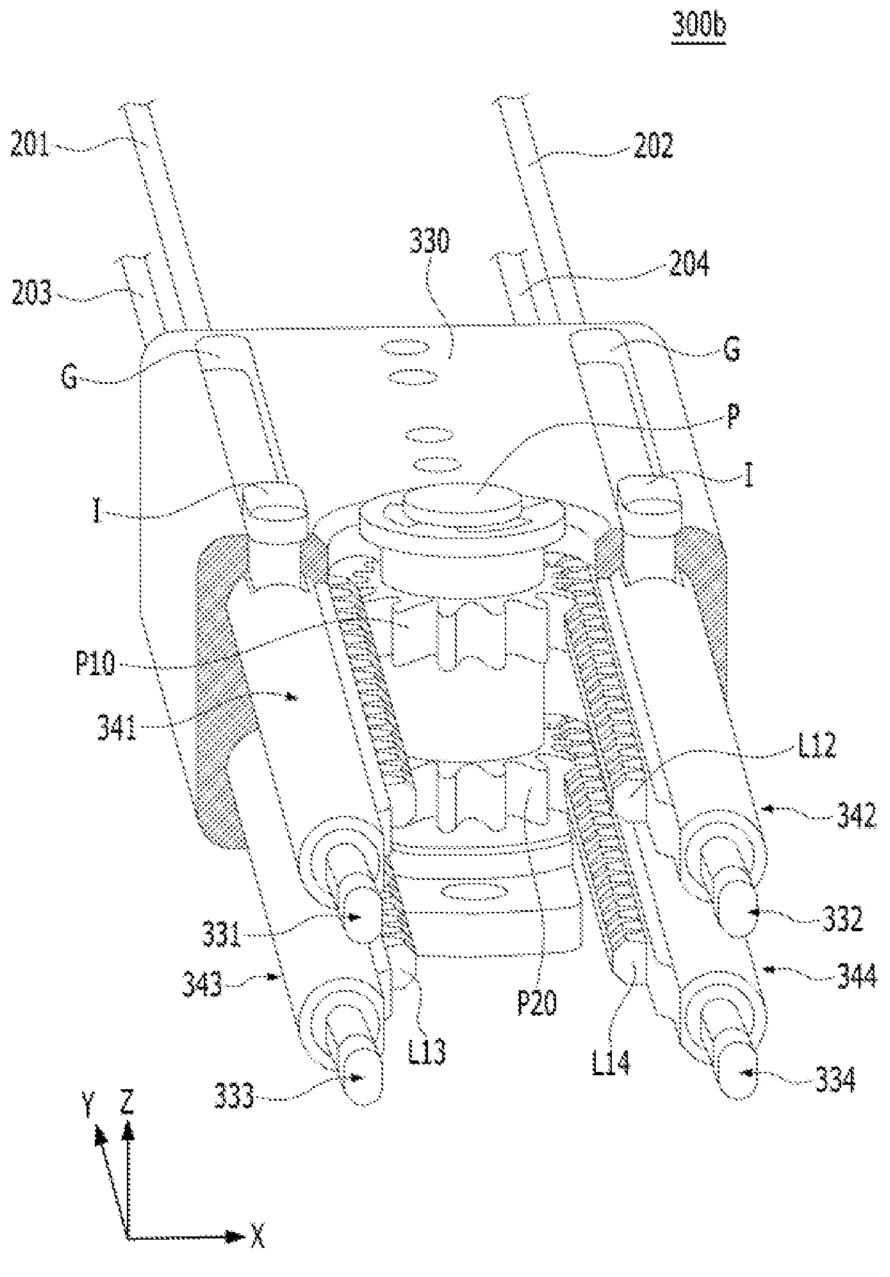
FIG. 4 is a perspective view showing a second detachment module included in a detachable endoscope according to an embodiment of the present disclosure.

FIG. 1 is a perspective view showing a detachable endoscope according to an embodiment of the present disclosure. FIG. 2 is a perspective view illustrating a detachment unit which couples an insertion unit and an operation unit that are provided in a detachable endoscope according to an embodiment of the present disclosure. FIG. 3 is a perspective view showing a detachment unit provided in a detachable endoscope according to an embodiment of the present disclosure. FIG. 4 is a perspective view showing a second detachment module included in a detachable endoscope according to an embodiment of the present disclosure.

Referring to FIGS. 1 to 4, a detachable endoscope 10 may be a device for inspecting and performing medical procedures on organs inside a body. In this case, the detachable endoscope 10 may include an operation unit 100, an insertion unit 200, and a detachment unit 300. Additionally, the detachable endoscope 10 may further include a joint unit 400. The joint unit 400 is electrically connected to an endoscope control and management system (not shown), and hereinafter, the operation unit 100, the insertion unit 200, and the detachment unit 300 will be mainly described.

The operation unit 100 is a part that the user manipulates to control the operation of the insertion unit 200, and may include an operation module H. In this case, the operation module H may include a lower operation part H10 and an upper operation part H20.

To one end (hereinafter, a first coupling end) of the operation unit 100, the detachable insertion unit 200 can be selectively connected. In the state in which the insertion unit 200 is coupled, the user can rotate the lower operation part H10 in left and right directions, so that the front end (hereinafter referred to as an insertion end) of the insertion unit 200 can be controlled to bend in up and down directions (direction A). Additionally, the user can control the insertion end of the insertion unit 200 to bend in left and right directions (direction B) by rotating the upper operation part H20 in left and right directions.

The upper operation part H20 may be provided with an upper sprocket (not shown), and an upper chain (not shown) meshed therewith, and the lower operation part H10 may be provided with a lower sprocket (not shown) and a lower chain (not shown) meshed therewith. In this case, when the upper operation part H20 and/or the lower operation part H10 are/is selectively rotated by the user's manipulation, the upper sprocket and/or the lower sprocket rotate(s), and this rotational motion can be converted into reciprocating rectilinear motion by the upper chain and/or the lower chain meshed therewith.

Additionally, the upper chain and the lower chain may be connected to the inside of the insertion end of the insertion unit 200 via connection wires 101, 102, 103, 104 and operation wires 201, 202, 203, 204, which will be described later. By the reciprocating rectilinear motion of the upper chain and/or the lower chain, the connection wires 101, 102, 103, 104 and the operation wires 201, 202, 203, 204 are selectively linearly moved, so that the insertion end of the insertion unit 200 connected to the operation wires 201, 202, 203, 204 can bend in the up and down directions (direction A) or in the left and right directions (direction B). Meanwhile, the user can adjust the bending amount of the insertion end by appropriately changing the rotation angle of the lower operation part H10 and/or the upper operation part H20.

Meanwhile, rotation of the upper sprocket and the lower sprocket may be made by the manual rotational manipulation of the user who holds the upper and lower operation parts H20 and H10 provided in the operation module H. However, the present disclosure is not limited to this, but each of the upper sprocket and the lower sprocket may also be constituted by connecting a rotational axle connected thereto with a driving means such as an electric motor, and using a separate remote control means for controlling the driving means.

A part (i.e., the insertion end) of the insertion unit 200 may be inserted into the body during an endoscopic procedure. In this case, the insertion end of the insertion unit 200 may be an end among both ends of the insertion unit 200, which is opposite to the end coupled to the operation unit 100 (hereinafter, referred to as a second coupling end). At the insertion end, an illuminating and photographing unit may be provided which has a light source for illuminating the inside of the body, and an image sensor for photographing the inside of the body.

The insertion end and its periphery of the insertion unit 200, in one embodiment, may have a long and thin cylindrical shape with a hollow formed therein. At least this portion of the insertion unit 200 may be formed with a flexible material, so that the bending direction can be adjusted by the operation unit 100 as described above. In the insertion unit 200, for example, a cover forming the outer surface of the insertion unit 200 may be formed with a flexible tube material such as a resin composition.

Meanwhile, the operation unit 100 may include a manipulation switch and a manipulation button for injecting or discharging liquid and gas used during an endoscopic procedure. A part (e.g., the second coupling end or its periphery) of the insertion unit 200 detachably coupled with the first coupling end of the operation unit 100 via the detachment unit 300 may be provided with an entrance through which a medical procedure tool such as an endoscopic procedure tool having a clip is protruded from or retracted into the insertion unit 200, and with a cap for opening and closing the entrance.

An air supply channel C30 for supplying air, a water supply channel C20 for supplying water, and a suction channel C10 for sucking in water and air and discharging them to the outside may be provided on the cover provided at the first coupling end of the operation unit 100. Additionally, the aforementioned cover may be provided with a terminal C40 electrically connected to the illuminating and photographing unit provided at the insertion end of the insertion unit 200.

The detachment unit 300 may detachably connect the operation unit 100 and the insertion unit 200. In this case, the detachment unit 300 may include a first detachment module **300*a* and a second detachment module 300*b* that are detachably coupled to each other, and by coupling or decoupling the first detachment module 300*a* and the second detachment module 300*b*, the operation unit 100 and the insertion unit 200** may be connected or separated.

The first detachment module **300*a* may be disposed to be inserted into the operation unit 100, and may include a first module body 310 and an intermediate connection part. At this time, the intermediate connection part may include two pairs of intermediate connection bodies 311, 312, 313, and 314, and connection ends E1, E2, E3, and E4 provided on the intermediate connection bodies 311, 312, 313, and 314, respectively. Meanwhile, hereinafter, the intermediate connection part will be denoted by reference numeral 320**, although this reference numeral is not shown in the drawings.

The first module body 310 may be a housing in which a middle hollow is formed penetrating both ends along the longitudinal direction (Y axis direction). Covers covering the middle hollow may be coupled to both ends of the first module body 310. In this case, the cover may be arranged on the same line with the middle hollow of the intermediate connection bodies 311, 312, 313, and 314 along the longitudinal direction (Y axis direction), and may have the through-holes 111, 112, 113, 114 (see FIG. 2) formed for connection communicating with the middle hollow.

The intermediate connection part 320 may connect the operation module H and the insertion end connection part 340 to be described later via the connection wires 101, 102, 103, and 104.

The intermediate connection bodies 311, 312, 313, and 314 may have various shapes. For example, the intermediate connection bodies 311, 312, 313, and 314 may be bars having an elongated cylindrical shape. The intermediate connection bodies 311, 312, 313, and 314 may be inserted penetrating the middle hollow of the first module body 310. In this case, the intermediate connection bodies 311, 312, 313, and 314 are inserted through the through-holes 111, 112, 113, 114 for connection of the first module body 310 and the covers coupled to both ends thereof, and accordingly, both ends of the intermediate connection bodies 311, 312, 313, and 314 may be disposed at least partially outside the first module body 310.

Engaging members 331, 332, 333, and 334 of the insertion end connection parts 340 may be detachably connected to the connection ends E1, E2, E3, and E4. The connection ends E1, E2, E3, and E4 may be disposed at one ends of the intermediate connection bodies 311, 312, 313, and 314, and these one ends of the intermediate connection bodies 311, 312, 313, and 314 may be ends among opposite ends of the intermediate connection bodies 311, 312, 313, and 314, which face the insertion unit 200. In this case, one ends of the connection wires 101, 102, 103, and 104 may be connected to the other ends of the intermediate connection bodies 311, 312, 313, 314, and the other ends of the connection wires 101, 102, 103, and 104 may be connected to upper chains or lower chains provided in the operation module H.

In this case, as the user manipulates the operation module H, the rotational motion of the upper sprockets or the lower sprockets can be converted into reciprocating rectilinear motion by the upper chains or the lower chains, and subsequently, the connection wires 101, 102, 103, and 104 connected to the upper chains or the lower chains may perform reciprocating rectilinear motion. Accordingly, the intermediate connection bodies 311, 312, 313, and 314 connected to the connection wires 101, 102, 103, and 104, and their connection ends E1, E2, E3, and E4 may perform reciprocating rectilinear motion along a direction parallel to the longitudinal direction (Y axis direction).

The connection ends E1, E2, E3, and E4 may be formed with a larger diameter than the outer diameter of the intermediate connection bodies 311, 312, 313, and 314. At this time, between the connection ends E1, E2, E3, and E4 and the connection wires 101, 102, 103, and 104, elastic members which the intermediate connection bodies 311, 312, 313, and 314 are inserted penetrating can be disposed. When the intermediate connection bodies 311, 312, 313, and 314 are pressed by the insertion end connection part 340 during the coupling process, the elastic members are compressed and deformed, and can generate an elastic restoring force for returning the intermediate connection bodies 311, 312, 313, and 314 to their original positions. The elastic member may be constituted with, for example, a coil spring.

The connection ends E1, E2, E3, and E4 may be provided with insertion grooves 321, 322, 323, and 324 into which the engaging members 331, 332, 333, and 334 are inserted when the insertion unit 200 and the operation unit 100 are coupled to each other, and guide projections T for guiding rotation of the intermediate connection bodies 311, 312, 313, and 314.

The insertion grooves 321, 322, 323, and 324 may be formed concavely in the longitudinal direction (e.g., −Y axis direction) inward from the connection ends E1, E2, E3, and E4. The insertion grooves 321, 322, 323, and 324 may be provided with penetration parts N formed to penetrate through the connection ends E1, E2, E3, and E4 in a direction (e.g., X axis direction) perpendicular to the longitudinal direction (Y axis direction). The insertion grooves 321, 322, 323, and 324 may be partially communicated with the outside through the penetration parts N. Additionally, the engaging members 331, 332, 333, and 334 can be in an engaged state and secured in the insertion grooves 321, 322, 323, and 324 by the penetration parts N.

The guide projections T1, T2, T3, and T4 can guide the rotational motion of the intermediate connection bodies 311, 312, 313, and 314. The guide projections T1, T2, T3, and T4 may be formed to protrude toward the outside in the radial direction from the connection ends E1, E2, E3, and E4 of the intermediate connection bodies 311, 312, 313, and 314.

When the insertion unit 200 and the operation unit 100 are coupled, and when the insertion end connection part 340 presses the connection ends E1, E2, E3, and E4 in the 'pressing direction (−Y axis direction)' parallel to the longitudinal direction, the guide projections T1, T2, T3, and T4 can move along guide slits G1, G2, G3, and G4 formed in the first module body 310.

The guide slits G1, G2, G3, and G4 may include a 'curved line part' that is curved and extended from one side of the first module body 310 to the other side thereof, and a 'straight line part' connected to this curved line part and extending backward (−Y axis direction) parallel to the longitudinal direction of the first module body 310.

In this case, when the connection ends E1, E2, E3, and E4 are pressed by the insertion end connection part 340, the guide projections T1, T2, T3, and T4 can be first rotated along the curved line part to guide the rotational motion of the intermediate connection bodies 311, 312, 313, and 314. Then, when the connection ends E1, E2, E3, and E4 are further pressed by the insertion end connection part 340, the guide projections T1, T2, T3, and T4 linearly can move along the straight line part to guide the intermediate connection bodies 311, 312, 313, and 314 to move along the pressing direction (−Y axis direction).

Meanwhile, the intermediate connection part 320 may include two pairs of intermediate connection bodies 311, 312, 313, and 314, and for the convenience of description, the two pairs of intermediate connection bodies 311, 312, 313 and 314 will be referred to as the first intermediate connection body 311, the second intermediate connection body 312, the third intermediate connection body 313, and the fourth intermediate connection body 314.

In this case, two pairs of middle hollows penetrating both ends may be formed in the first module body 310 along the longitudinal direction (Y axis direction). The first, second, third, and fourth intermediate connection bodies 311, 312, 313, and 314 may be respectively inserted penetrating the two pairs of middle hollows.

The first, second, third, and fourth intermediate connection bodies 311, 312, 313, and 314 may be arranged symmetrically with each other, within the first module body 310, in the width direction (X axis direction) and/or in the height direction (Z axis direction).

Specifically, the first intermediate connection body 311 may be arranged symmetrically with the second intermediate connection body 312 in the width direction (X axis direction). At this time, the first intermediate connection body 311 may be arranged symmetrically with the third intermediate connection body 313 in the height direction (Z axis direction), and the third intermediate connection body 313 may be arranged symmetrically with the fourth intermediate connection body 314 in the width direction (X axis direction). Accordingly, the first intermediate connection body 311 and the second intermediate connection body 312 can be arranged side by side in a pair on the upper side inside the first module body 310, and the third intermediate connection body 313 and the fourth intermediate connection body 314 can be arranged side by side in a pair on the lower side inside the first module body 310.

Respective connection ends of the first, second, third, and fourth intermediate connection bodies 321, 322, 323, and 324, that is, the first connection end E1, the second connection end E2, the third connection end E3, and the fourth connection end E4 are inserted to penetrate the through-holes 111, 112, 113, and 114 for connection provided in the cover, respectively, so that they can protrude outward toward the insertion unit 200 from the first module body 310.

Additionally, the first connection wire 101, the second connection wire 102, the third connection wire 103, or the fourth connection wire 104 may be connected to the other ends of the first, second, third, and fourth intermediate connection bodies 311, 312, 313, and 314, respectively, opposite to the connection ends E1, E2, E3, and E4. In this case, each of the intermediate connection bodies 311, 312, 313, and 314 may be inserted penetrating the inside of the elastic member in the form of a coil spring.

The second detachment module 300*b* may be arranged to be inserted into the insertion unit 200, and may include a second module body 330 and an insertion end connecting part. At this time, the insertion end connection part may include the two pairs of insertion end connection bodies 341, 342, 343, and 344, and the engaging members 331, 332, 333, 334 provided at the insertion end connection bodies 341, 342, 343, 344, respectively. Meanwhile, hereinafter, the insertion end connection part will be denoted by reference numeral 340, although this reference numeral is not shown in the drawings.

The second module body 330 may be a housing having an insertion end hollow which penetrates both ends thereof along the longitudinal direction (Y axis direction).

The insertion end connection part 340 can transfer the force applied by the user's manipulation of the operation module H to the insertion end via the operation wires 201, 202, 203, and 204, so that the insertion end can bend.

The insertion end connection bodies 341, 342, 343, and 344 may have a variety of shapes. For example, the insertion end connection bodies 341, 342, 343, and 344 may be bars having an elongate cylindrical shape. The insertion end connection bodies 341, 342, 343, and 344 may be inserted penetrating the insertion end hollow of the second module body 330. At this time, both ends of the insertion end connection bodies 341, 342, 343, and 344 may be disposed at least partially outside the second module body 330.

Each of the insertion end connection bodies 341, 342, 343, and 344 may have a rack gear part L11, L12, L13, or L14 on its one surface. Each of the rack gear parts L11, L12, L13, and L14 may be disposed on the surface among the surfaces of each of the insertion end connection bodies 341, 342, 343, and 344, which faces the center of the second module body 330, and the insertion end connection body 341, 342, 343, and 344 may extend in the longitudinal direction (Y axis direction).

The engaging members 331, 332, 333, and 334 may be inserted into the aforementioned insertion grooves 321, 322, 323, and 324 of the connection ends E1, E2, E3, and E4, and may be detachably coupled thereto.

The engaging members 331, 332, 333, and 334 may be disposed at one ends of the insertion end connection bodies 341, 342, 343, and 344, and the one ends of the insertion end connection bodies 341, 342, 343, and 344 may be ends facing the operation unit 100. In this case, one ends of the operation wires 201, 202, 203, and 204 may be connected to the other ends of the insertion end connection bodies 341, 342, 343, and 344, and the other ends of the operation wires 201, 202, 203, and 204 may be connected to the inside of the insertion ends.

Meanwhile, the insertion end connection parts 340 may include two pairs of insertion end connection bodies 341, 342, 343, and 344. For the convenience of description, the two pairs of insertion end connection bodies will be referred to as the first insertion end connection body 341, the second insertion end connection body 342, the third insertion end connection body 343, and the fourth insertion end connection body 344.

In this case, the second module body 330 may be formed so as to have two pairs of insertion end hollows penetrating both ends along its longitudinal direction (Y axis direction). The first, second, third, and fourth insertion end connection bodies 341, 342, 343, and 344 may be respectively arranged to be inserted penetrating the two pairs of insertion end hollows.

The first, second, third, and fourth insertion end connection bodies 341, 342, 343, and 344 may be arranged symmetrically with each other in the width direction (X axis direction) and/or the height direction (Z axis direction) in the second module body 330.

Specifically, the first insertion end connection body 341 may be arranged symmetrically with the second insertion end connection body 342 in the width direction (X axis direction). Accordingly, the first rack gear part L11 of the first insertion end connection body 341 and the second rack gear part L12 of the second insertion end connection body 342 may be arranged to face each other. Additionally, the first insertion end connection body 341 may be arranged symmetrically with the third insertion end connection body 343 in the height direction (Z axis direction), and the third insertion end connection body 343 may be arranged symmetrically with the fourth insertion end connection body 344 in the width direction (X axis direction). Accordingly, the third rack gear part L13 of the third insertion end connection body 343 and the fourth rack gear part L14 of the fourth insertion end connection body 344 may be arranged to face each other. Accordingly, the first insertion end connection body 341 and the second insertion end connection body 342 can be arranged side by side in a pair on the upper side inside the second module body 330, and the third insertion end connection body 343 and the fourth insertion end connection body 344 can be arranged side by side in a pair on the lower side inside the second module body 330.

In the above-described case, the second module body 330 may be provided with a pinion gear part P which rotates around a rotational axle extending through and between the first insertion end connection body 341 and the second insertion end connection body 342, and between the third insertion end connection body 343 and the fourth insertion end connection body 344. In this case, the pinion gear part P may include a first pinion gear P10 and a second pinion gear P20.

The first pinion gear P10 may be disposed between the first insertion end connection body 341 and the second insertion end connection body 342, so that it can be meshed with the first rack gear part L11 and the second rack gear part L12 at the same time. In this meshed state, the first pinion gear P10 may rotate around the first central axle part perpendicular to the longitudinal direction (Y axis direction) according to the user's manipulation of the operation module H.

The second pinion gear P20 may be disposed between the third insertion end connection body 343 and the fourth insertion end connection body 344, so that it can be meshed with the third rack gear part L13 and the fourth rack gear part L14 at the same time. In this meshed state, the second pinion gear P20 may rotate around the second central axle part perpendicular to the longitudinal direction (Y axis direction) according to the user's manipulation of the operation module H.

The second central axle part may be disposed on the same line as the first central axle part, but may be configured to be separated from each other and independently rotatable. Accordingly, while the first pinion gear P10 and the second pinion gear P20 rotate around the first central axle part or the second central axle part, they can avoid interfering (or hindering) each other's rotational movements.

The second module body 330 may have 'straight line guide slits G' extending in the longitudinal direction (Y axis direction) on its upper and lower surfaces. The straight line guide slits G may be provided in a pair on the upper surface of the second module body 330 to face the first insertion end connection body 341 and the second insertion end connection body 342, respectively, and may also be provided in a pair on the lower surface of the second module body 330 to face the third insertion end connection body 343 and the fourth insertion end connection body 344, respectively.

In this case, the first insertion end connection body 341 and the second insertion end connection body 342 may each be provided with 'guide protruding members I' extending upward and inserted into the straight line guide slits G facing each other. And, the third insertion end connection body 343 and the fourth insertion end connection body 344 may each be provided with guide protruding members I extending downward and inserted into the straight line guide slits G facing each other. In this case, the guide protruding member I moves along the linear guide slit G, so that it can guide the reciprocating rectilinear motion of each connected insertion end connection body.

At one end of each of the first, second, third, and fourth insertion end connection bodies 341, 342, 343, and 344, the first engaging member 331, the second engaging member 332, the third engaging member 333, or the fourth engaging member 334 may be provided. And, to the other end of each of the first, second, third, and fourth insertion end connection bodies 341, 342, 343, and 344, the first operation wire 201, the second operation wire 202, the third operation wire 203, or the fourth operation wire 204 may be connected.

Figure 5:
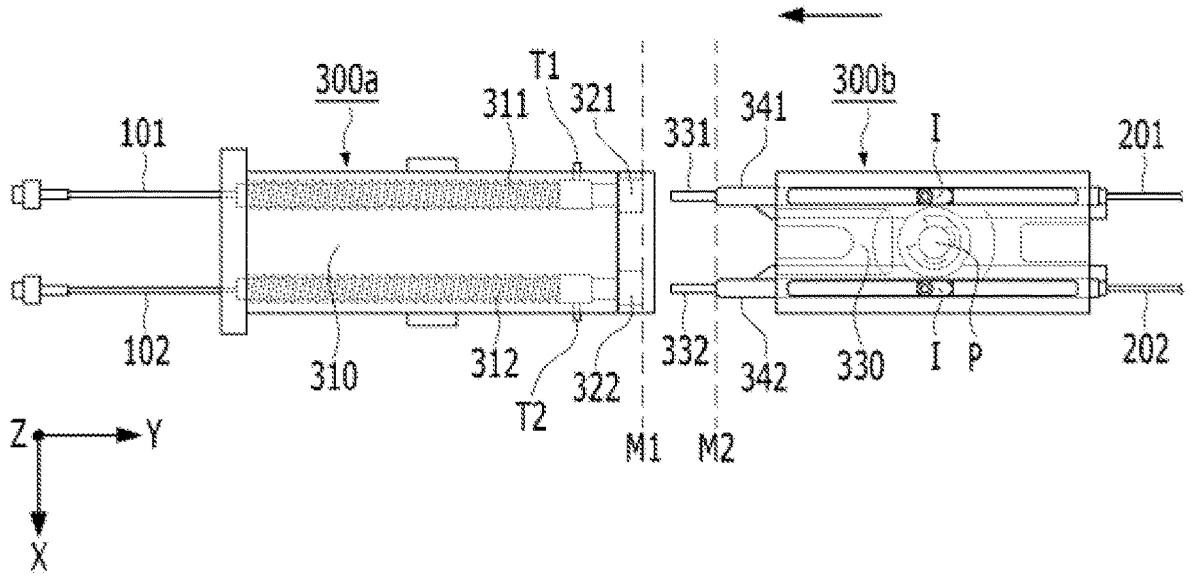
FIG. 5 is a plan view showing a state before the insertion unit and the operation unit are coupled through the detachment unit according to an embodiment of the present disclosure.
Figure 6:
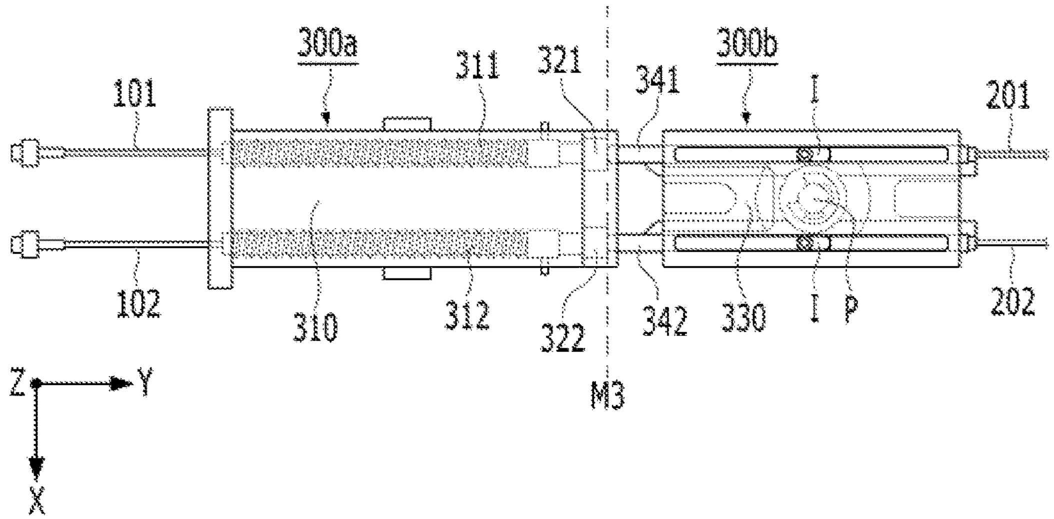
FIG. 6 is a plan view showing a state in which the insertion unit and the operation unit are coupled through a detachment unit according to an embodiment of the present disclosure.

FIG. 5 is a plan view showing a state before the insertion unit and the operation unit are coupled through the detachment unit according to an embodiment of the present disclosure. FIG. 6 is a plan view showing a state in which the insertion unit and the operation unit are coupled through a detachment unit according to an embodiment of the present disclosure.

Referring to FIGS. 5 and 6, a method of arranging and combining the operation unit 100 and the insertion unit 200 may be as follows.

First, the first coupling end of the operation unit 100 and the second coupling end of the insertion unit 200 may be disposed to face each other. As an example, before coupling, the first coupling end of the operation unit 100 may be in a 'parallel-aligned state' with the second coupling end of the insertion unit 200.

Here, when viewing the detachable endoscope 10 from above based on the Z axis of the drawing, the 'parallel-aligned state' may mean a state in which the virtual first reference line M1 connecting the first connection end E1 and the second connection end E2 [and connecting the third connection end E3 and the fourth connection end E4] provided in the operation unit 100 is parallel to the virtual second reference line M2 connecting one end of the first insertion end connection body 341 and one end of the second insertion end connection body 342 [and connecting one end of the third insertion end connection body 343 and one end of the fourth insertion end connection body 344] provided in the insertion unit 200.

Next, the operation unit 100 and the insertion unit 200 can be moved in a direction parallel to the longitudinal direction (Y axis direction) and approaching each other (hereinafter, referred to as a coupling direction). In this case, since the insertion unit 200 and the operation unit 100 are in a 'parallel-aligned state', the first engaging member 331 and the second engaging member 332 of the insertion unit 200 may be inserted into the first insertion groove 321 of the first connection end E1 and the second insertion groove 322 of the second connection end E2, respectively, while at the same time maintaining a parallel state to each other. In addition, the third engaging member 333 and the fourth engaging member 334 of the insertion unit 200 may also be inserted into the third insertion groove 323 of the third connection end E3 and the fourth insertion groove 324 of the fourth connection end E4, respectively, while at the same time maintaining a state parallel to each other, and to the first engaging member 331 and the second engaging member 332.

In this case, as the operation unit 100 and the insertion unit 200 move in the coupling direction (Y axis direction), the engaging members 331, 332, 333, and 334 can be completely inserted into the insertion grooves 321, 322, 323, and 324, and ends of the insertion end connection bodies 341, 342, 343, and 344 can contact the connection ends E1, E2, E3, and E4 facing them. Accordingly, the first connection end E1 and the second connection end E2 [and the third connection end E3 and the fourth connection end E4] may be arranged to pass a virtual third reference line M3 together with one end of the first insertion end connection body 341 and one end of the second insertion end connection body 342 [and one end of the third insertion end connection body 343 and one end of the fourth insertion end connection body 344].

Next, when the intermediate connection part 320 moves backward (in the −Y axis direction) by the user's manipulation of the operation module H, the connection ends E1, E2, E3, and E4 and the intermediate connection bodies 311, 312, 313, and 314 may move backward (−Y axis direction) while rotating by the guide projections T1, T2, T3, and T4 and the guide slits G1, G2, G3, and G4. With this, the engaging members 331, 332, 333, and 334 may be secured to one ends of the insertion grooves 321, 322, 323, and 324 in the engaged state, so that the insertion unit 200 and the operation unit 100 can be coupled with each other. In this regard, the specific combination method will be described in detail below.

Meanwhile, as another embodiment, the first coupling end may be in 'a misaligned state' with the second coupling end before the coupling. Here, the 'misaligned state' may refer to a state in which, when the detachable endoscope 10 is viewed from above, one end of the first insertion end connection body 341 and one end of the second insertion end connection body 342 protrude at different distances, so that the first reference line M1 and the second reference line M2 are not parallel to each other and are inclined at a predetermined angle.

This 'misaligned state' may be a state in which some of the insertion end connection bodies 341, 342, 343, and 344 may protrude further toward the operation unit 100 than the rest of the insertion end connection bodies. For example, it may be a state in which one end of the first insertion end connection body 341 protrudes further toward the operation unit 100 than one end of the second insertion end connection body 342, and the other insertion end connection bodies 343 and 344.

Next, the operation unit 100 and the insertion unit 200 may be moved to approach each other in a direction parallel to the longitudinal direction (Y axis direction) (hereinafter, referred to as a coupling direction). At this time, since the insertion unit 200 and the operation unit 100 are in 'the misaligned state', the first engaging member 331 of the insertion unit 200 can begin to be inserted into the first insertion groove 321 of the first connection end E1 earlier before the second engaging member 332 as well as the other engaging members 333 and 334.

In this case, as the operation unit 100 and the insertion unit 200 move along the coupling direction, the first locking member 331 can be first fully inserted into the first insertion groove 321, so that the one end of the first insertion end connection body 341 can come into contact with the first connection end E1 facing the first insertion end connection body 341. At this time, the second insertion end connection body 342 and the other insertion end connection bodies 343 and 344 may be in a non-contact state with the connection ends E2, E3, and E4 facing them, or in a state in which only a portion of the engaging member is inserted into the insertion groove.

Next, the operation unit 100 and the insertion unit 200 move further in the coupling direction (Y axis direction), and the first intermediate connection part 320 in contact with the first insertion end connection body 341 is pressed, so that it can be moved backward (−Y axis direction).

In this case, the other insertion end connection bodies 342, 343, and 344 may sequentially contact the connection ends E2, E3, and E4 facing them, respectively, based on the distances protruding toward the operation unit 100. At the same time, as the respective connection ends are pressed, the elastic members provided in the intermediate connection bodies 311, 312, 313, and 314 can be compressed and deformed at the same time or at the different times, and the intermediate connection bodies 311, 312, 313, and 314 can be moved in the coupling direction (Y axis direction), respectively. Accordingly, all the elastic members can be pressed until they reach the 'same compression deformation state'. Here, the same compression deformation state may refer to a state in which the elastic members have the same or similar compressed length and shape after their deformation.

When all the elastic members are in the same compression deformation state, all the insertion end connection bodies 341, 342, 343, and 344 may come into contact with the facing connection ends E1, E2, E3, and E4, respectively. In this case, the first connection end E1 and the second connection end E2 [and the third connection end E3 and the fourth connection end E4] are arranged to pass the virtual third reference line M3 together with one end of the first insertion end connection body 341 and one end of the second insertion end connection body 342 [and one end of the third insertion end connection body 343 and one end of the fourth insertion end connection body 344], and thus, the first coupling end of the operation unit 100 and the second coupling end of the insertion unit 200 can be in a 'parallel-aligned state' as described above.

Then, the operation unit 100 and the insertion unit 200 move further in the coupling direction, so that they can press the connection ends E1, E2, E3, and E4 backward (i.e., −Y axis direction) while maintaining contact with the insertion end connection bodies 341, 342, 343, and 344. Accordingly, the intermediate connection bodies 311, 312, 313, and 314 connected to the connection ends E1, E2, E3, and E4 are rotated by the guide projections T1, T2, T3, and T4 and the guide slits G1, G2, G3, and G4, so that the engaging members 331, 332, 333, and 334 can be inserted into the insertion grooves 321, 322, 323, and 324, and secured by being engaged with one ends of the insertion grooves 321, 322, 323, and 324. Accordingly, the insertion unit 200 may be coupled to the operation unit 100.

Figure 7A:
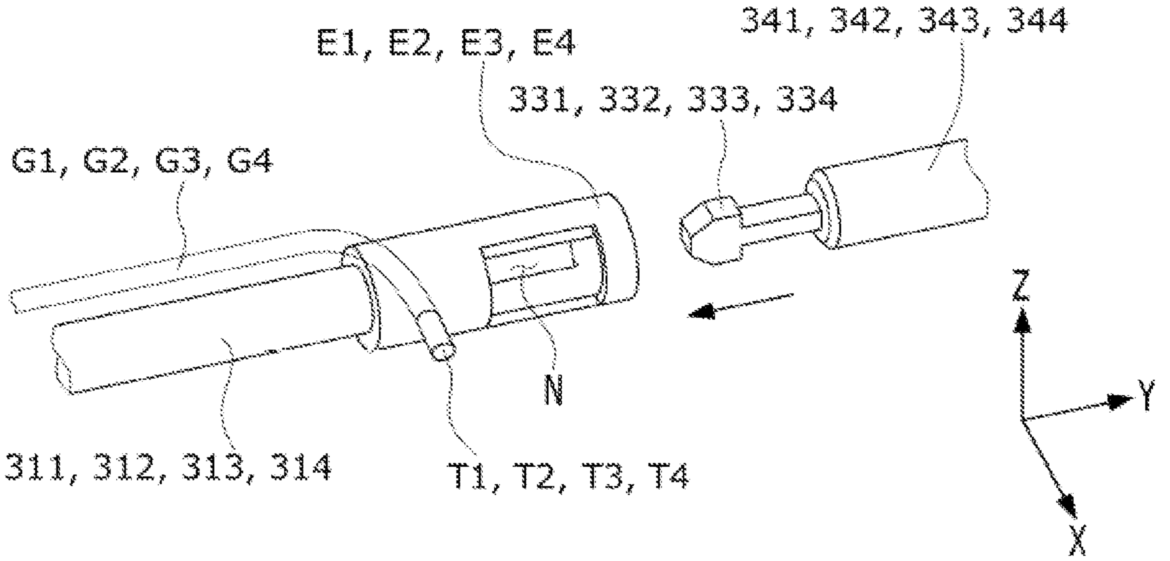
FIG. 7A is a perspective view showing a state before the intermediate connection part and the insertion end connection part provided in the detachable endoscope according to an embodiment of the present disclosure are coupled to each other.
Figure 7B:
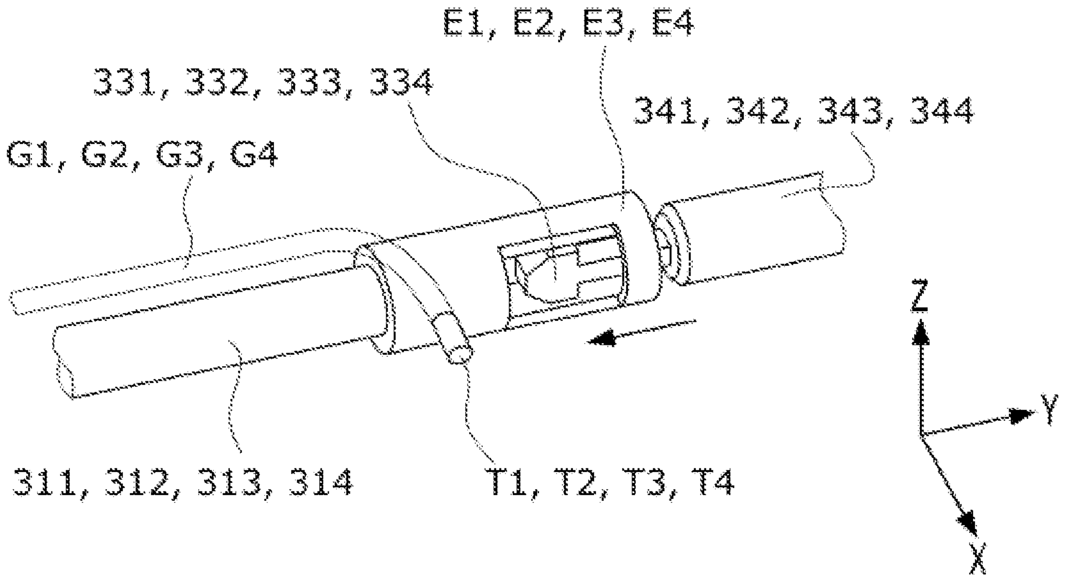
FIGS. 7B and 7C are perspective views showing states before the coupling of the intermediate connection part and the insertion end connection part is completed.
Figure 7C:
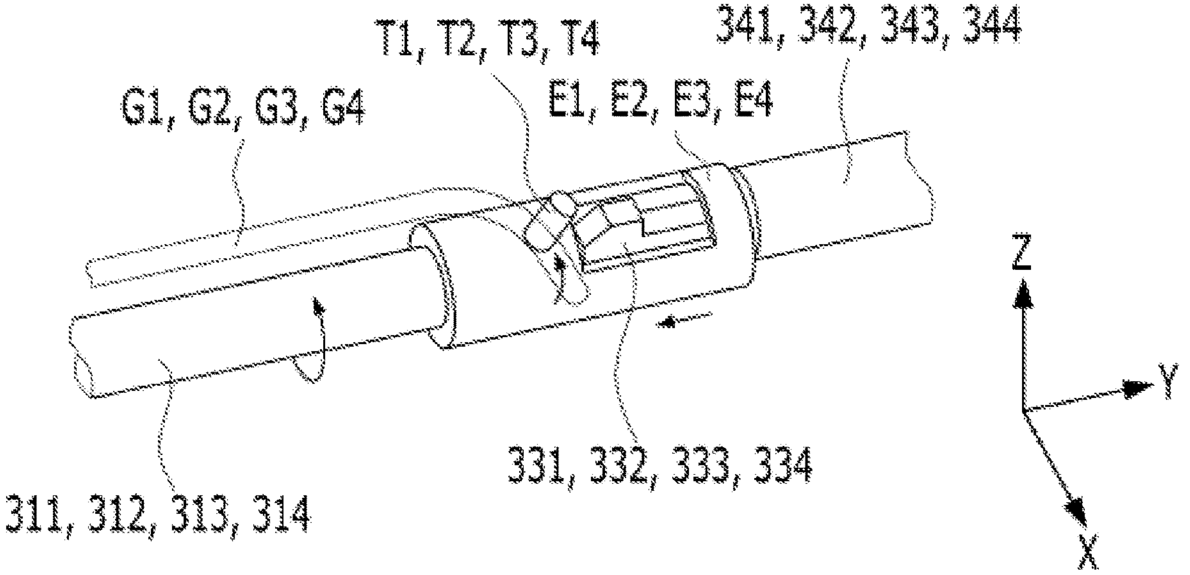
Figure 7D:
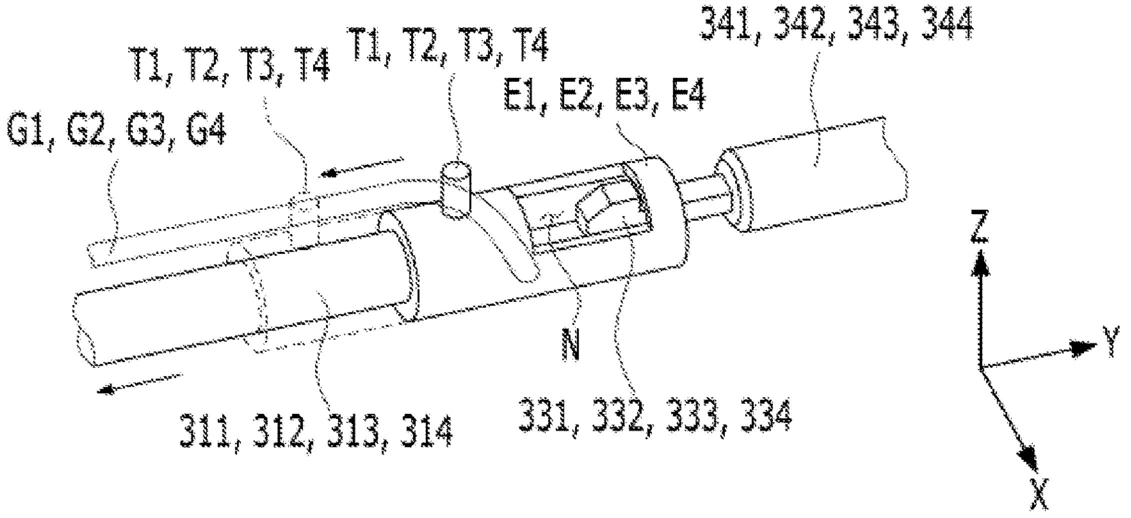
FIG. 7D is a perspective view showing a state in which the intermediate connection part and the insertion end connection part are coupled.
Figure 8A:
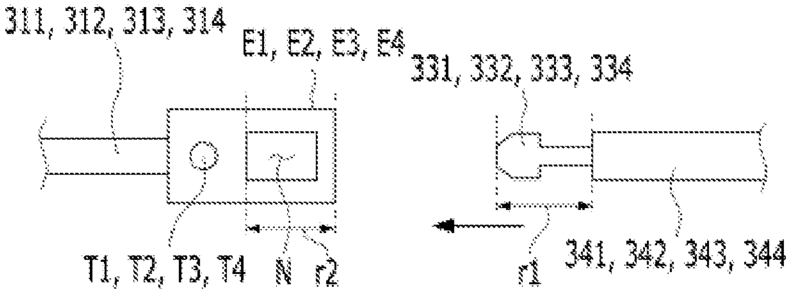
FIG. 8A is a side view of FIG. 7A.
Figure 8B:
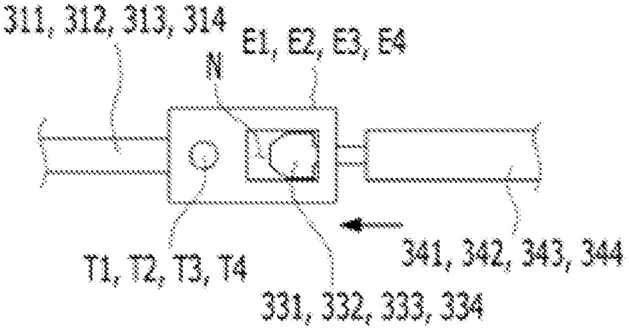
FIG. 8B is a side view of FIG. 7B.
Figure 8C:
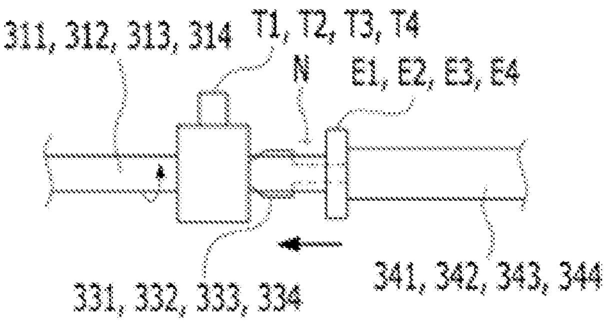
FIG. 8C is a side view of FIG. 7C.
Figure 8D:
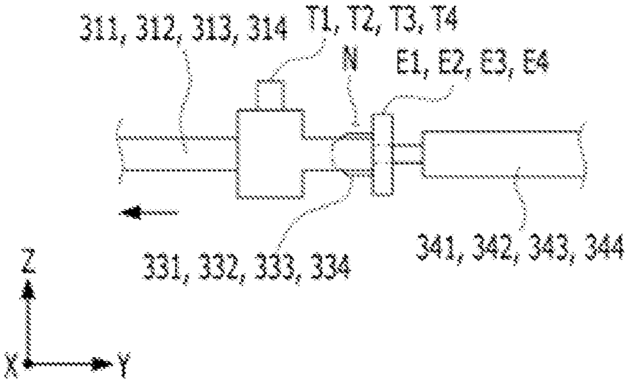
FIG. 8D is a side view of FIG. 7D.

FIG. 7A is a perspective view showing a state before the intermediate connection part and the insertion end connection part provided in the detachable endoscope according to an embodiment of the present disclosure are coupled to each other. FIGS. 7B and 7C are perspective views showing states before the coupling of the intermediate connection part and the insertion end connection part is completed. FIG. 7D is a perspective view showing a state in which the intermediate connection part and the insertion end connection part are coupled.

Referring to FIGS. 7A to 7D, and FIGS. 8A to 8D, a method of coupling the insertion end connection part 340 to the intermediate connection part 320 may be as follows.

First, as described above, before the coupling, the operation unit 100 and the insertion unit 200 are arranged to face each other, so that the intermediate connection part 320 and the insertion end connection part 340 may be arranged to face each other. At this time, in a state where the connection ends E1, E2, E3, and E4 face the engaging members 331, 332, 333, and 334 each other, the intermediate connection bodies 311, 312, 313, and 314 may be arranged on the same line as the insertion end connection bodies 341, 342, 343, and 344 in the longitudinal direction (Y axis direction) (see FIGS. 7A and 8A).

Next, the operation unit 100 and the insertion unit 200 may be moved so as to come closer along the coupling direction. In this case, the engaging members 331, 332, 333, and 334 can be inserted into the insertion grooves 321, 322, 323, and 324 provided at the connection ends E1, E2, E3, and E4.

At this time, the engaging members 331, 332, 333, and 334 may be provided with an 'engaging projection' protrudingly formed toward the outer side of the radial direction of the engaging members 331, 332, 333, and 334 at their front ends. When the engaging members 331, 332, 333, and 334 are inserted into the insertion grooves 321, 322, 323, and 324, the engaging projections may be accommodated in the insertion grooves 321, 322, 323, and 324 (see FIGS. 7B and 8B).

Next, as the insertion unit 200 moves further along the coupling direction (Y axis direction), the front ends of the insertion end connection bodies 341, 342, 343, and 344 may come into contact with the connection ends E1, E2, E3, and E4.

In this regard, the protruding distance r1 of the engaging members 331, 332, 333, and 334 may be formed to be similar to (preferably, shorter in length than) the depth r2 of the insertion grooves 321, 322, 323, and 324. Accordingly, when the front ends of the insertion end connection bodies 341, 342, 343, and 344 come into contact with the connection ends E1, E2, E3, and E4, the front ends of the engaging members 331, 332, 333, and 334 can be in a non-contact state (i.e., a predetermined gap exists) with the inside of the insertion grooves 321, 322, 323, and 324.

Next, the user may operate a locking part 200*a* provided at the second coupling end of the insertion unit 200 to couple and fix the insertion unit 200 to the operation unit 100. As an example, the locking part 200*a* may be rotatably installed at the second coupling end, and the first coupling end of the operation unit 100 may be inserted into this locking unit 200*a*. In this case, as the user rotates the locking part 200*a* in one direction, the locking part 200*a* and the first coupling end may be coupled in a screw connection method and secured together.

In this regard, when the locking part 200*a* is rotated, the insertion end connection bodies 341, 342, 343, and 344 are further moved in the coupling direction (−Y axis direction) in a state of being in contact with the connection ends E1, E2, E3, and E4, so that they can press the connection ends E1, E2, E3, and E4 and the intermediate connection bodies 311, 312, 313, and 314 backward (−Y axis direction). With this, the guide projections T1, T2, T3, and T4 move backward (−Y axis direction) while rotating along the 'curved line parts' of the guide slits G1, G2, G3, and G4, and as a result, the connection ends E1, E2, E3, and E4 and the intermediate connection bodies 311, 312, 313, and 314 can be rotated around the longitudinal direction (Y axis direction).

By this rotation, in a state where the engaging members 331, 332, 333, and 334 are accommodated in the insertion grooves 321, 322, 323, and 324, the engaging projections protrude to the outside of the insertion grooves 321, 322, 323, and 324 through the penetration part N to be in a non-separable state (primary coupling state) (see FIG. 7C).

Next, in the primary coupling state, by the user's manipulation of the operation module H, the intermediate connection part 320 can be pulled backward (−Y axis direction). In this case, the guide projections T1, T2, T3, and T4 pass through the 'curved line parts' of the guide slits G1, G2, G3, and G4 and move backward (in the −Y axis direction) along the 'straight line parts,' and accordingly, the engaging projections of the engaging members 331, 332, 333, and 334 protruding outward through the penetration part N can be in the engaged state at the inner ends of the insertion grooves 321, 322, 323, and 324. As a result, the intermediate connection part 320 and the insertion end connection part 340 may be coupled to become a non-separable state (secondary coupling state)(see FIG. 7D). Thereafter, in the 'secondary coupling state', by the user's manipulation of the operation module H, the intermediate connection part 320 and the insertion end connection part 340 can perform reciprocating rectilinear motion and operate integrally.

Meanwhile, when removal or replacement of the insertion unit 200 is required, the insertion unit 200 may be separated from the operation unit 100 by a process as follows.

First, reference points (not shown) provided respectively on the first operation part H10 and the second operation part H20 may be aligned in a line. In this way, when the first and second operation parts H10 and H20 are aligned along the reference points, the operation unit 100 and the insertion unit 200 may again be in a 'parallel-aligned state' as described above.

Next, the locking state may be released by rotating the locking part 200*a* of the insertion unit 200 in a direction opposite to the locking direction. After the unlocking of the locking part 200*a* is completed, the user may separate the insertion unit 200 by moving it away from the operation unit 100 in a direction opposite to the coupling direction (Y axis direction). Thereafter, the replacement of the insertion unit 200 may be completed by coupling another insertion unit as a replacement to the operation unit 100 through the same or similar method as described above.

Regarding the operation method of the detachable endoscope 10 as described above, when the insertion unit 200 and the operation unit 100 are assembled in the 'second coupled state', by the user's manipulation of the first operation part H10 or the second operation part H20, the intermediate connection part 320 performs reciprocating rectilinear motion through the lower sprocket and the upper sprocket, and the lower chain and upper chain respectively connected thereto, and at this time, the insertion end connection part 340 can perform reciprocating rectilinear motion integrally with the intermediate connection part 320 while being coupled with it through the engaging members 331, 332, 333, and 334 and the insertion grooves 321, 322, 323, and 324, respectively.

In this case, the first detachment module 300*a* may be connected to the operation module H through the lower sprocket and the upper sprocket rotated in forward/backward directions by the first and second operation parts H10 and H20, the lower chain and the upper chain connected thereto to be wound around them, and the first, second, third and fourth connection wires 101, 102, 103 and 104 connected to both ends of the chains.

The first and second connection wires 101 and 102 connected to both ends of the upper chain connected to the upper sprocket operate in linkage with the first and second operation wires 201 and 202 disposed side by side in a pair on the upper side of the inside of the insertion unit 200 based on the drawing, so that the first and second connection wires can bend the insertion end of the insertion unit 200 in the left and right directions (direction B).

Contrarily, the third and fourth connection wires 103 and 104 connected to both ends of the lower chain connected to the lower sprocket to be wound around it operate in linkage with the third and fourth operation wires 203 and 204 disposed side by side in a pair on the lower side of the inside of the insertion unit 200 based on the drawing, so that the third and fourth connection wires can bend the insertion end of the insertion unit 200 in the up and down directions (direction A). However, the present disclosure is not limited to this, and bending manipulations in the up and down directions (direction A) and the left and right directions (direction B) may be reversed depending on the design of the detachable endoscope 10.

As described above, in the detachable endoscope 10 according to the embodiments of the present disclosure, the insertion unit 200 intended to be inserted into the human body is configured to be detachable from the operation unit 100, so that the internal contamination of the endoscope 10 can be prevented and parts can be easily replaced and cleaned. Additionally, in the course of coupling the insertion unit 200, one end of the insertion unit 200 can be inserted into and pressed against one end of the operation unit 100, and at the same time, engaged, coupled, and locked therewith, without the use of a separate engaging or locking structure, thereby enabling simple and easy assembly and disassembly of the insertion unit 200.

The afore-mentioned description of the disclosure is just an example, and a person having ordinary skill in the art may understand that it can be easily modified into other specific configuration without changing the technical spirit or essential features of the disclosure. Accordingly, it should be understood that the embodiments described above are illustrative in every respect and not restrictive. For example, the respective components described as a singular form may be implemented in a distributed form, and likewise the respective components described as a distributed form may be implemented in a combined form.

The scope of the present disclosure is represented by the following claims, and all modifications and changes derived from the meaning and scope of the claims and equivalent concepts thereof should be interpreted as being included in the scope of the present disclosure.

REFERENCE SIGN LIST

10: Detachable endoscope
100: Operation unit
200: Insertion unit
300: Detachment unit
300*a*: First detachment module
300*b*: Second detachment module
400: Joint unit

What is claimed is:

1. A detachable endoscope, comprising:

an insertion unit having a first end and a second end, the first end being configured to be inserted into a body;

an operation unit configured to be coupled to the second end of the insertion unit, the operation unit having an operation module having a sprocket, the operation unit being configured to bend the first end of the insertion unit in response to actuation of the operation module;

a locking part rotatably disposed at the second end of the insertion unit and configured to screw-couple the insertion unit and the operation unit to each other upon rotation of the locking part; and a detachment unit configured to detachably couple the operation unit and the insertion unit to each other, wherein the detachment unit includes:

a first detachment module disposed at one end of the operation unit, the first detachment module having an intermediate connection part and a connection wire configured to receive a force from the operation module; and a second detachment module disposed at the second end of the insertion unit and configured to be detachably coupled to the first detachment module, the second detachment module having an insertion end connection part and an operation wire configured to transfer the force from the operation module to the first end of the insertion unit, wherein the insertion end connection part includes:

an insertion end connection body extending along a first longitudinal axis thereof, the insertion end connection body having a first end and a second end opposite to the first end, the second end of the insertion end connection body being connected to the operation wire; and an engaging member protruding along the first longitudinal axis from the first end of the insertion end connection body, the engaging member having an end and an engaging projection projecting radially outward with respect to the first longitudinal axis, wherein the intermediate connection part includes:

an intermediate connection body extending along a second longitudinal axis thereof and being rotatable about the second longitudinal axis and having a first end configured to face the first end of the insertion end connection body, wherein the intermediate connection body defines:

an insertion groove recessed from the first end of the intermediate connection body along the second longitudinal axis;

a penetration part having a hole extending through a sidewall of the insertion groove, wherein when the insertion unit and the operation unit are screw-coupled, the engaging member is configured to be inserted into the insertion groove, and the first end of the insertion end connection body is configured to contact the first end of the intermediate connection body, wherein a protruding distance of the engaging member is shorter than a depth of the insertion groove, such that a contact of the first end of the insertion end connection body with the first end of the intermediate connection body defines a maximum insertion depth of the engaging member into the insertion groove at which the end of the engaging member is spaced apart from a base surface of the insertion groove by a gap, wherein the insertion end connection body is configured to, upon the rotation of the locking part, press the first end of the intermediate connection body along the second longitudinal axis and thereby rotate the intermediate connection body about the second longitudinal axis and move the engaging projection outward through the penetration part into an engaged state in which the insertion end connection part and the intermediate connection part are non-separable.

2. The detachable endoscope of claim 1, wherein the intermediate connection part further includes:

a guide projection configured to guide a rotational motion of the intermediate connection body.

3. The detachable endoscope of claim 2, wherein as the intermediate connection body rotates with the guide projection when the intermediate connection part is pressed by the insertion end connection part, the engaging member is configured to be inserted into the hole of the penetration part to be in an engaged state.

4. The detachable endoscope of claim 1, wherein the intermediate connection part and the insertion end connection part are configured to be coupled to each other while being arranged on a same line along a fourth longitudinal direction to face each other and operate integrally based on manipulation of the operation module.

* * * * *